United States Patent [19]

Swartz

[11] Patent Number: 5,344,459
[45] Date of Patent: Sep. 6, 1994

[54] ARTHROSCOPICALLY IMPLANTABLE PROSTHESIS

[76] Inventor: Stephen J. Swartz, 603 Harding Rd., Little Silver, N.J. 07739

[21] Appl. No.: 32,713

[22] Filed: Mar. 17, 1993

Related U.S. Application Data

[63] Continuation of Ser. No. 802,055, Dec. 3, 1991, abandoned.

[51] Int. Cl.⁵ ............................................. A61F 2/30
[52] U.S. Cl. ........................................ 623/18; 623/20
[58] Field of Search ............... 623/8, 11, 17, 20, 18

[56] References Cited

U.S. PATENT DOCUMENTS

| 3,638,536 | 2/1972 | Klenwachter et al. | |
|---|---|---|---|
| 3,750,194 | 8/1973 | Summers | 623/11 |
| 4,183,102 | 1/1980 | Guiset | 623/1 |
| 4,502,161 | 3/1985 | Wall | |
| 4,578,082 | 3/1986 | Sen-Jung | |
| 4,796,603 | 1/1989 | Dahlke et al. | 623/11 |
| 4,919,667 | 4/1990 | Richmond | |
| 4,919,668 | 4/1990 | Rosenbaum et al. | |
| 4,932,969 | 6/1990 | Frey et al. | 623/17 |

Primary Examiner—David Isabella
Assistant Examiner—Debra S. Brittingham
Attorney, Agent, or Firm—Klauber & Jackson

[57] ABSTRACT

A prosthetic device is described which is arthroscopically implantable into a joint, which can restore function to a diseased joint, alleviating the need for joint therapy.

The device has a ring or a pair of rings sized and shaped to fit within the joint. The ring or rings are comprised of a polymeric substance and may contain one or more compartments which are inflatable or expandable with air, a liquid or a semi-solid, through an arthroscope coupling means.

12 Claims, 9 Drawing Sheets

ARTHROSCOPICALLY IMPLANTABLE PROSTHESIS

This application is a continuation of application Ser. No. 07/802,055, filed Dec. 3, 1991 abandoned.

BACKGROUND OF THE INVENTION

This application relates to an inflatable prosthesis which is implantable arthroscopically. The prosthesis is primarily useful in weight-bearing joints, such as the knee joint, for individuals who have experienced joint damage due to inflammation, degeneration or trauma. Additionally, the prosthesis is useful palliatively in failing joints in patients who are essentially unable to tolerate joint replacement surgery and the rehabilitation which is necessary thereafter.

U.S. Pat. No. 4,932,969 (Frey, et al.) issued Jun. 12, 1990 relates to a joint endoprosthesis used as an intervertebral spacer and as a spacing prosthesis in other joints, such as the wrist. A toroidal ring defining an annular cavity is mentioned therein, having a plurality of partitions for an incompressible fluid medium. The ring is covered by a reinforcing material which is attached to mating contoured shells.

U.S. Pat. No. 4,502,161 (Wall) issued Mar. 5, 1985 relates to a prosthetic substitute for natural menisci or cartilage found in and around joints. The prosthesis comprises a body portion formed of a resilient material such as Teflon ® and a strut which is attached to the bone outside of the joint. The reinforcing material, such as a mesh of Nylon ®, is embedded within both members.

U.S. Pat. No. 4,919,667 (Richmond) issued Apr. 24, 1990 relates to a soft tissue implant in the form of a meniscus cartilage replacement. The implant is anatomically-shaped three-dimensionally like the natural medial meniscus cartilage of a natural joint. Thus, a generally C-shaped implant having a wedge shape in central cross section is shown. The implant is formed of a multi-layer laminate body and a porous tube bonded to a thick edge of the body. The tube permits fibrous tissue ingrowth after implant.

U.S. Pat. No. 4,183,102 (Guiset) issued Jan. 15, 1980 relates to an inflatable prosthetic device for lining a body duct, such as an artery or vein. The device comprises a generally toroidal, hollow, inflatable sleeve, the outer portions of which conform to the shape of the interior wall portion of a duct. A plurality of these sleeves may be connected if appropriate in a side by side relationship. The sleeves are intended for use in lining the wall portions of the duct, and the center channel formed thereby permits the passage of liquid.

U.S. Pat. No. 4,919,668 (Rosenbaum, et al.) issued on Apr. 24, 1990 relates to a prosthetic replacement for a disc in the human jaw. The temporomandibular implant functionally replaces an irreparable temporomandibular disc. The prosthetic device utilizes a compressible pouch-like container containing a resilient material which encloses a matrix of open cell material.

U.S. Pat. No. 4,578,082 (Sen-Jung) issued Mar. 25, 1986 relates to a fluid cushion apparatus which acts as a pivoting mechanism which can be incorporated into an artificial limb, such as an artificial leg.

U.S. Pat. No. 3,638,536 (Kleinwachter, et al.) issued Feb. 1, 1972 relates to a pressurizable variable capacity chamber for transforming fluid pressure into motion. The device contains a stretchable bag-shaped diaphragm attached to at least two rigid relatively immovable members, and can be used in an artificial arm as a fluid-driven muscle.

OBJECTS OF THE INVENTION

One object of the present invention is to provide an implantable prosthetic device which can be inserted into joints, in particular the knee joint, and inflated arthroscopically with air or another gas, liquid, a settable solid or a semi-solid such as a gel.

Another object of the present invention is to provide an implantable prosthetic device which does not require inflation or filling with a gas, liquid, semi-solid or settable gel.

Another object of the present invention is to provide a prosthetic device which is readily tolerated by patients with degenerative joint diseases when the prosthesis is in place.

Yet another object of the present invention is to provide a device which is easily implanted and disconnected from an arthroscope.

These and other objects will be obvious to those of ordinary skill in the art from the teachings herein.

SUMMARY OF THE INVENTION

An arthroscopically implantable prosthetic device is disclosed for implantation into a mammalian joint, most preferably a knee joint. The device is comprised of at least one annularly-shaped ring, sized and shaped to fit within said joint. The ring is comprised of a polymeric material which is essentially non-irritating to the surrounding tissues, and which allows said joint to flex without causing any substantial irritation or inflammation.

One embodiment of the invention utilizes the ring or rings in solid or semi-solid form, without the need for inflation or filling thereof. This configuration utilizes a polymeric material with or without a sealed cavity in the interior thereof.

Alternatively, the ring or rings may contain at least one, and preferably a plurality of compartments in the interior thereof, which can be filled with a substance, thus expanding said compartments or reducing the compressibility of said ring or rings during use. Also included is a means for filling said compartments with said substance which is in communication with said compartment or compartments.

Alternatively, a plurality of annularly-shaped rings can be joined together laterally or vertically and sized in combination to fit within said joint. The rings again can be comprised of a polymeric material which is non-irritating and which allows the joint to flex during use without substantial irritation. The rings may be solid or semi-solid throughout, and may contain a single compartment or a plurality of compartments in any one of numerous different configurations, which can be hollow or filled with a substance as described above.

Preferably the substance used to fill the compartments is air, a liquid or a polymeric gel which is injected via the arthroscope into the compartment or compartments contained within the ring or rings after the device has been surgically implanted and is properly situated in the joint.

BRIEF DESCRIPTION OF THE DRAWINGS

The invention is described in detail in connection with the drawings appended hereto, wherein.

DETAILED DESCRIPTION OF THE INVENTION

The prosthesis described herein is used to provide pain relief, support, mobility and correction of joint angulation, primarily, but not exclusively for the knee. The device is a temporizing measure which is useful in certain clinical situations, such as in painful or failing joints, or in those patients not able to tolerate or substantially benefit from joint replacement therapy.

As used herein, the compartments contained within the prosthetic device are referred to as "fillable" or "expandable". This means that the compartments may be filled fully or partially with air or a non-reactive gas, water or another inert liquid or a settable solid or semi-solid, such as a gel which is non-hardening or hardening to the desired level of stiffness. In this manner, the compartments can be filled to capacity or proper stiffness without requiring that the compartments enlarge, such as could occur if elastic were used.

Alternatively, the device may utilize one or a number of annularly shaped rings which are solid, semi-solid or spongy without the need for inflation, filling or expansion with a substance. In this instance, the device can utilize a sealed hollow cavity or a sealed cavity filled with a substance or alternatively can utilize varying layers or regions which have differing levels of stiffness or compressibility, or can be essentially uniform in its stiffness or compressibility throughout. The stiffness can be uniform laterally as well as in a cross-section.

Additionally, if the stiffness is to be varied laterally, this may be accomplished through the use of a heat-set or other curable polymer which can be treated prior to implantation to effect the appropriate stiffness in one portion of the device while leaving the other portions of the ring or rings in their pre-treated condition.

Referring in detail to the drawings, one embodiment of the invention is the device shown generally as 20. The prosthesis is comprised of a single annular ring which may contain one or a plurality of compartments which are collapsible, inflatable or expandable as described in detail below.

The device in this configuration is typically comprise of a tough, outer polymeric material 21 the outer material may be abrasion resistant. Materials suitable for use as the outer polymeric material include but are not limited to polyethylene, polypropylene, polyurethane and polybutyl rubber, with the most preferred being polypropylene.

Preferably the material used on the outer surface of the device is non-irritating to the joint and will permit the joint to flex adequately without pain and irritation. Therefore, a somewhat smooth outer surface is desirable and the device would remain flexible or pliable much as a cushion upon expansion of the compartments contained in the device.

The rings can be supported or strengthened using reinforcing fibers 22. Such fibers can be comprised of any suitable material and can woven or otherwise attached to the polymeric material.

The fibers typically are arranged radially around the upper and lower surfaces of the ring or rings for added strength. Since these fibers typically do not stretch, the device can be expanded to a point where the body of the ring becomes harder and more rigid.

When a plurality of annularly-shaped rings is used, the rings can be joined by a central section 23 which can be comprised of the same polymeric material used on the outer surface of each ring. Also, the central section may contain one or more inflatable or expandable compartments as described above, and may contain a plurality of fibers which reinforce the connection between the rings.

Figure 5:
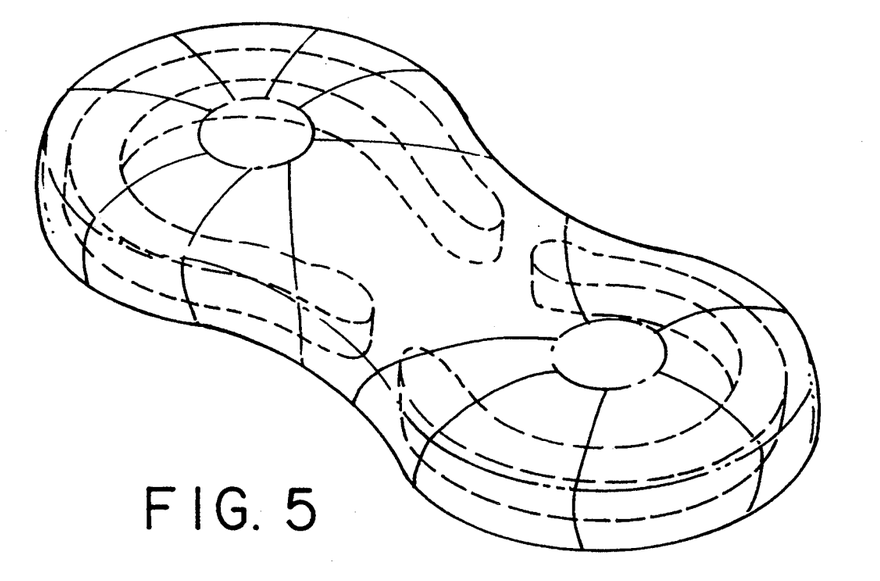
FIG. 5 is an implantable prosthetic device comprised of a pair of annularly-shaped rings joined laterally containing a pair of compartments on the interior thereof.
Figure 6:
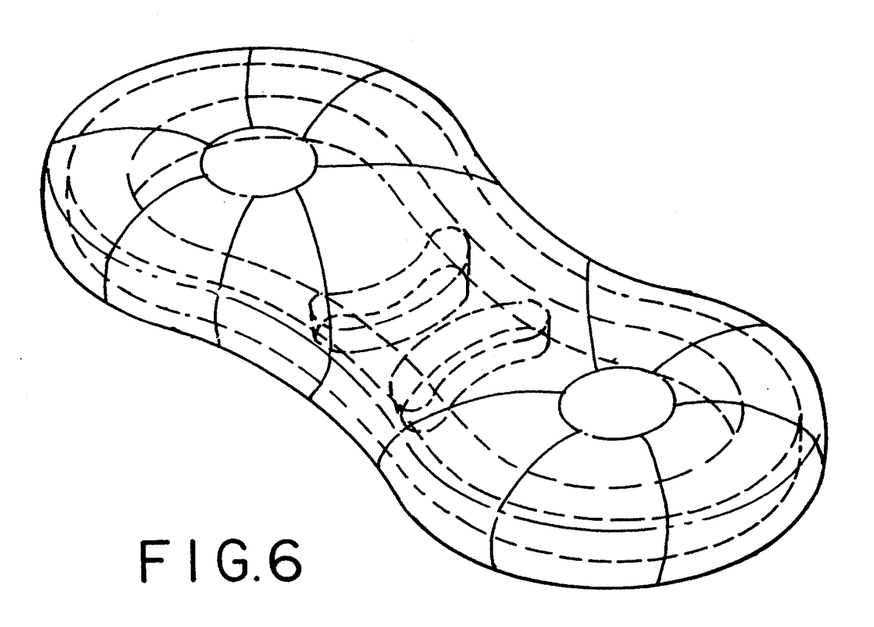
FIG. 6 is a perspective view of a prosthetic device having a pair of rings and three compartments.
Figure 7:
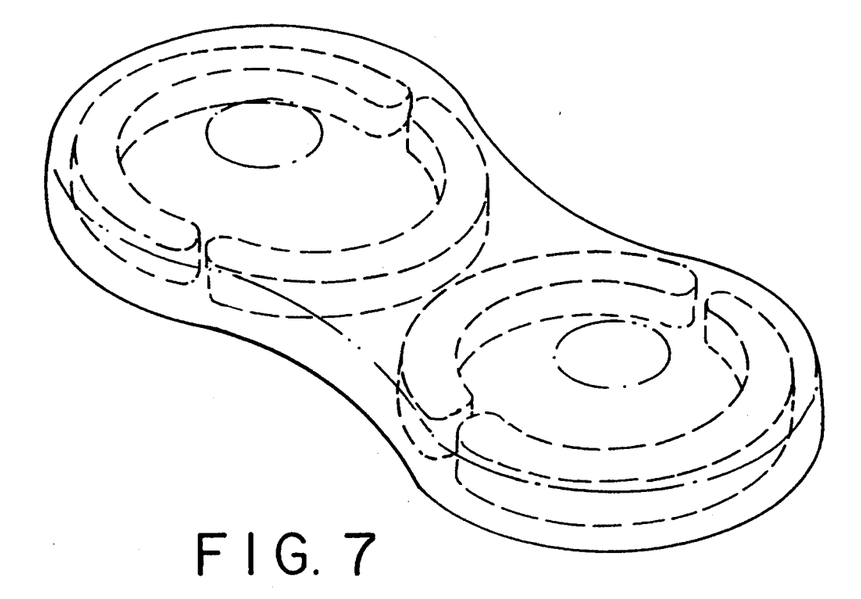
FIG. 7 is an alternative configuration of an implantable prosthetic device containing two annularly-shaped rings joined laterally containing four compartments.
Figure 8:
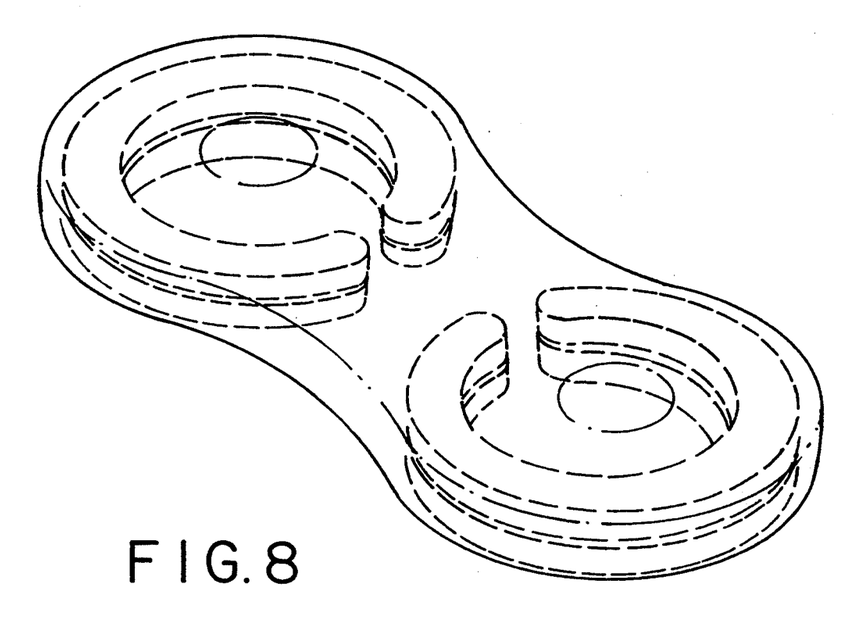
FIG. 8 is an alternative embodiment of the implantable prosthetic device shown in FIGS. 5–7, containing two compartments.
Figure 9:
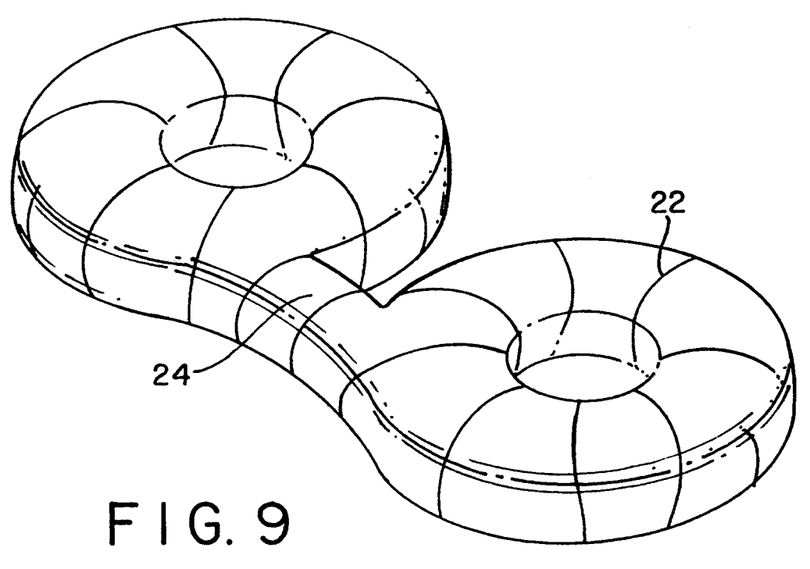
FIG. 9 is another alternative configuration of the implantable prosthetic device containing a pair of annularly-shaped rings joined laterally with part of the lateral section removed.
Figure 10:
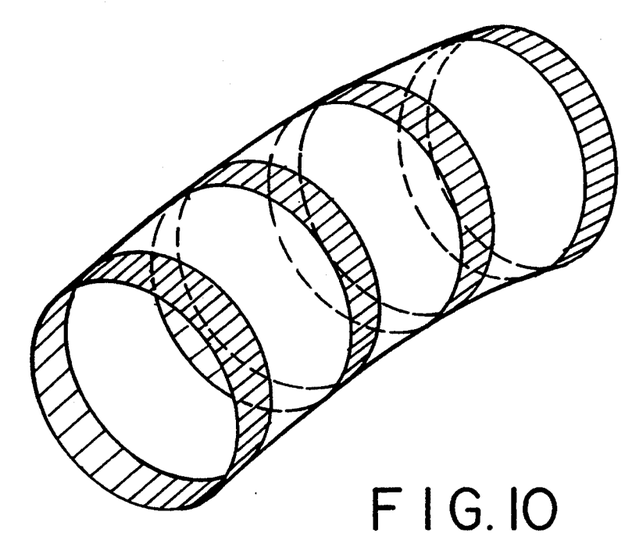
FIG. 10 is a cross-sectional view of a segment of an annularly-shaped implantable prosthetic device, displaying the septated walls of the expandable compartment.

Typically the lateral section 23 joins a pair of rings evenly as shown in FIG. 5. However, in an alternative embodiment of the invention, the lateral section need not be evenly distributed front to back as shown in FIG. 9. In this configuration, the lateral section 24 does not constrain the cruciate ligaments during use. This non-ligament constraining embodiment of the lateral section is useful when said ligaments are in place and are left undamaged, thus holding the joint together.

The compartment or compartments used in the implantable prosthetic device described herein are inflatable with air or another gas, or expandable with water or another liquid, or with a semi-solid, such as the gel as described above.

Figure 1:
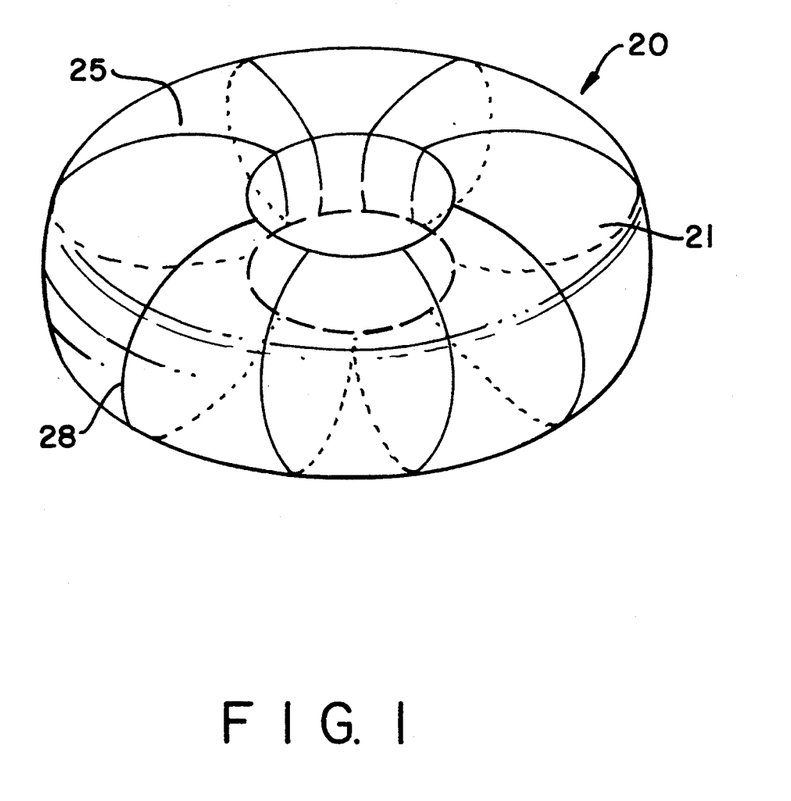
FIG. 1 is a perspective view of the prosthetic device utilizing a single annularly-shaped ring solid or semi-solid throughout or containing a single compartment.

In its most preferred form, a single annularly-shaped prosthetic device contains a single compartment 25. As noted above, single ring devices are most useful when the cruciate ligaments are intact and are healthy, thus adding further support for the knee. In this fashion, a pair of single annularly-shaped devices may be implanted, left and right, into each joint using left and right incisions and employing otherwise standard arthroscopic surgical techniques.

Figure 2:
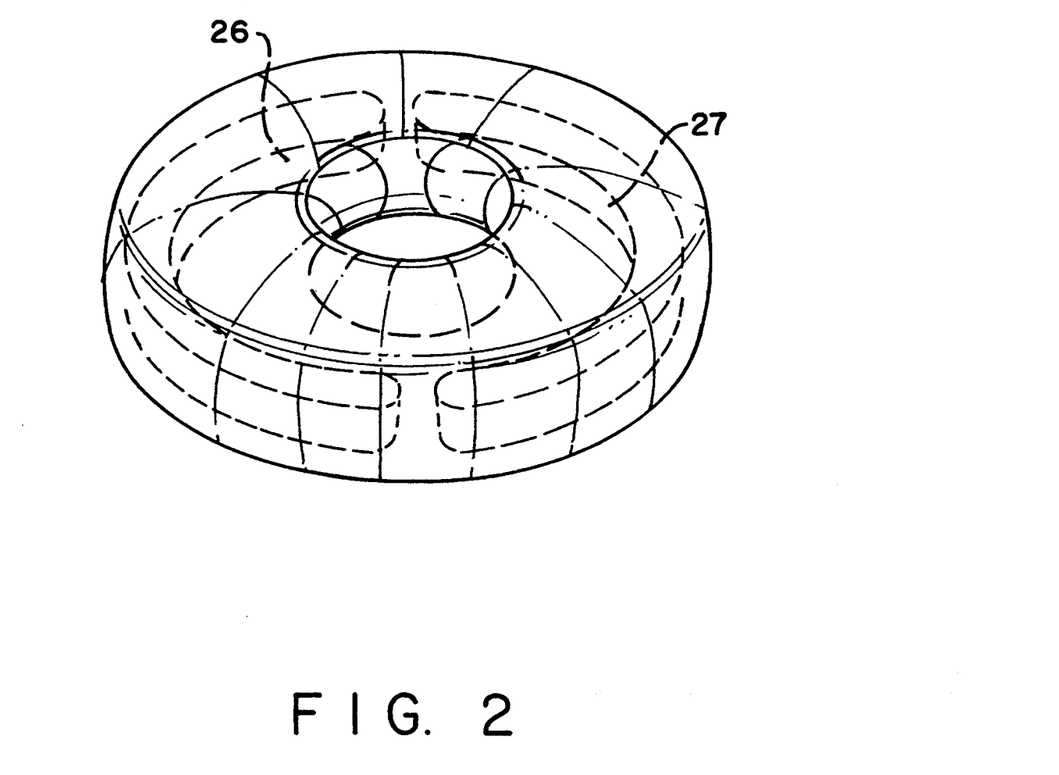
FIG. 2 is a perspective view of the prosthetic device utilizing a single annularly-shaped ring containing a pair of fillable compartments.
Figure 3:
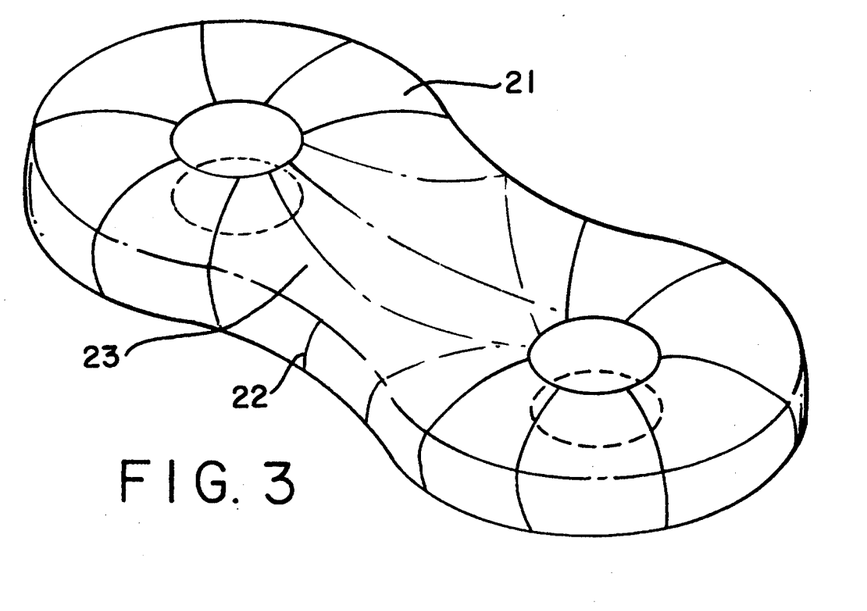
FIG. 3 is a prosthetic device comprised of a pair of annularly-shaped rings which contain one compartment.
Figure 4:
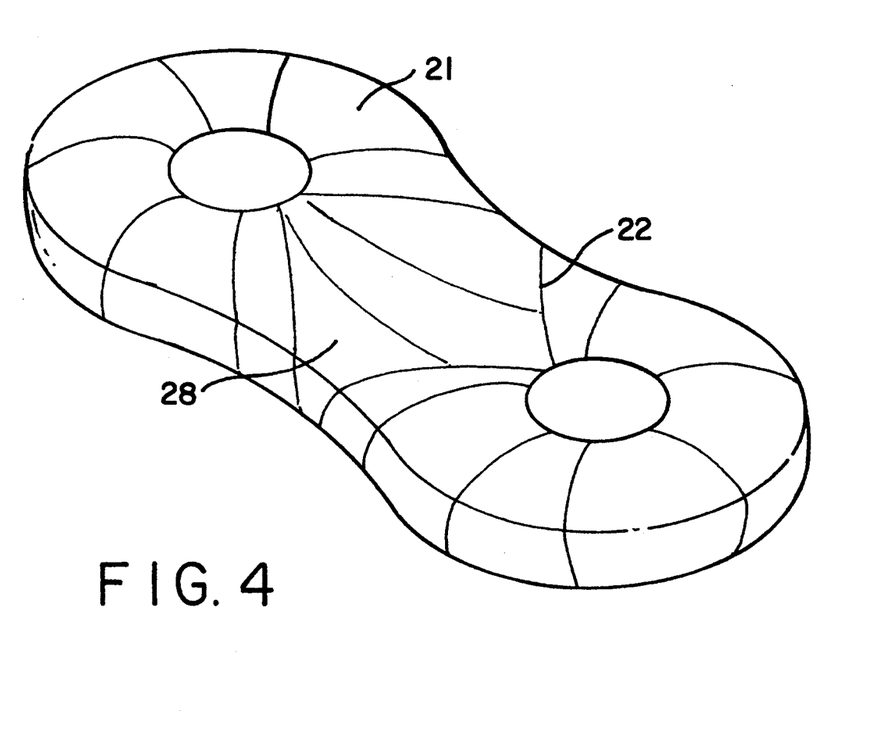
FIG. 4 is a perspective view of the prosthetic device comprised of a pair of annularly-shaped rings joined laterally which are solid or semi-solid throughout.

Alternatively, in the single annularly-shaped ring, when a number of compartments is contained therein, such as shown in FIG. 2, bilateral compartments 26 and 27 are preferred, as shown. In the preferred configuration, a plurality of compartments is present.

In the multiple (lateral) ring configuration, the single compartment 28 utilized may span both rings as well as the lateral section contained between the rings. Alternatively, a plurality of inflatable or expandable compartments can be contained therein, as shown in FIGS. 5-8 and 11.

The compartment or multiple compartments contained within the ring or rings, as well as any compartments contained within the lateral portion between the rings may all be comprised of the same or different material from that which covers the outer surface of the device. For example, a polymerizing rubber elastomer can be included such that upon introduction of the substance which will fill the compartment or compartments, said compartments can expand and yet the device remains suitably pliable during use.

Preferably the material used for inflating or expanding the compartments is a gel which partially hardens or can be cured to form a semi-solid which is radiopaque, such that the device can be easily located upon x-raying the joint. When the device is constructed without the inflatable compartments a radiopaque material can be incorporated into the polymeric material from which the device is constructed.

Most preferably, the inflatable compartments are septated to provide internal strength, and each compartment is independently inflated or expanded through its own tube or valve through a coupler on the exterior of the device which is connected to the arthroscope during insertion of the device into the joint. Inflation typically proceeds from the most distal to the most proximal compartment. Adjustments in height, size and angulation can be made by differentially inflating the compartments, and upon flexion and extension of the leg or other limb. Movement can thus be corrected if appropriate.

Figure 11:
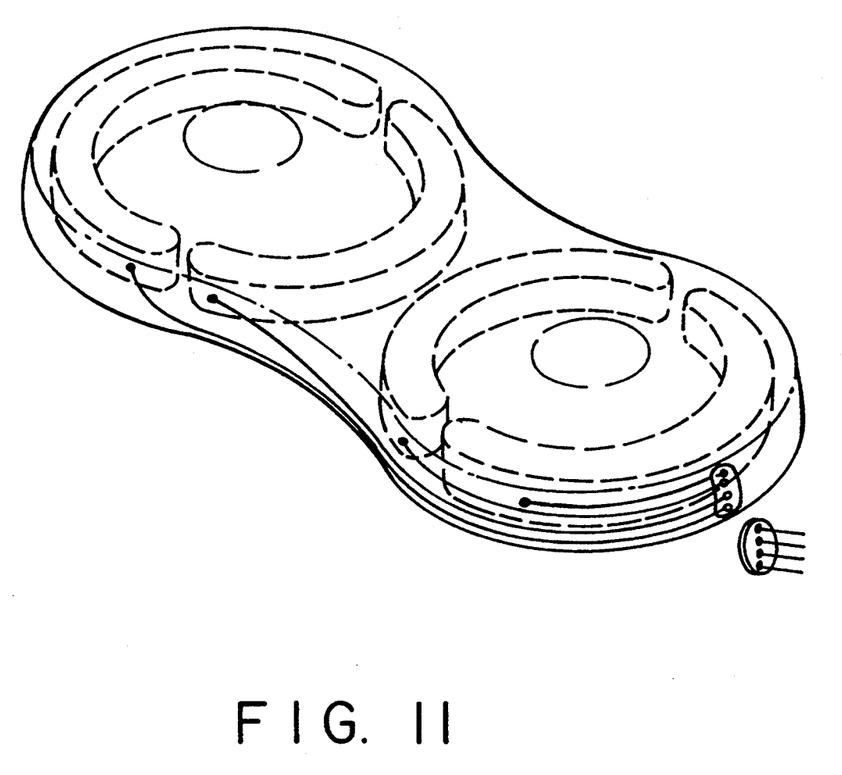
FIG. 11 is a diagram showing a coupler which is used to attach the implantable prosthetic device to an arthroscope by which the device is inserted into a joint and by which the compartments are expanded.
Figure 12:
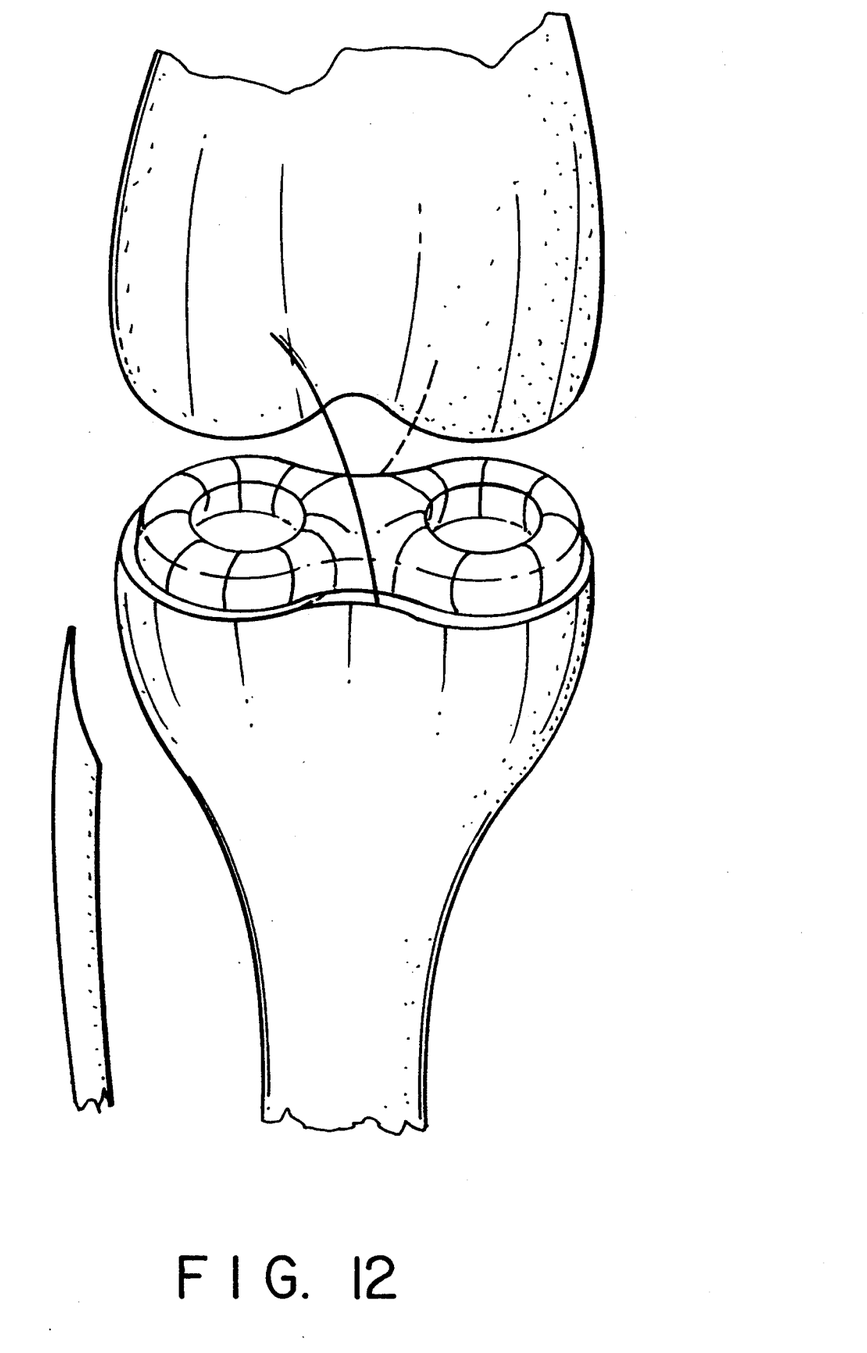
FIG. 12 is a drawing of the implantable prosthetic device in place in a knee joint, wherein the device is comprised of a pair of annularly-shaped rings joined laterally.
Figure 13:
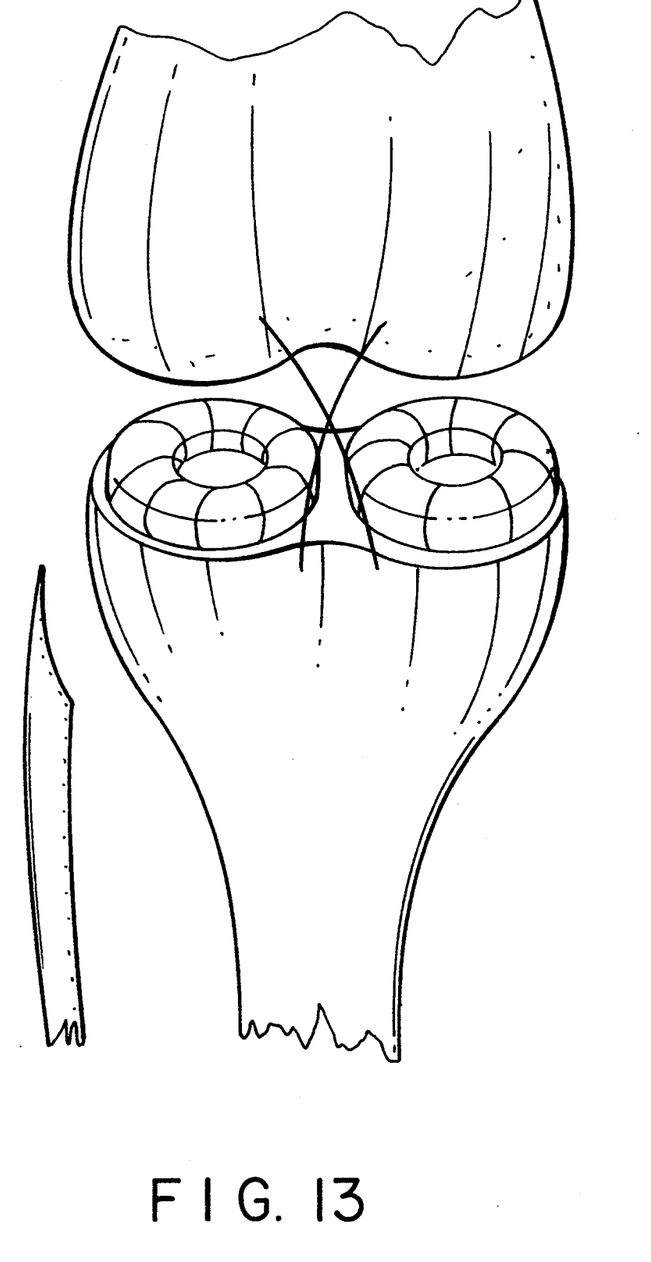
FIG. 13 is a diagram of a pair of implantable prosthetic devices in place in a knee joint with the cruciate ligaments intact.

Each of the compartments is connected to an inflation or expansion tube next to the coupler the means for filling the at least one compartment may be comprised of at least one line suitable for passing the substance into the compartment. The coupler in turn attaches to the arthroscope The coupler allows inflation of each compartment with air or the preferred gel. Once the connecting tube is uncoupled from the arthroscope, such as by a twisting action, the coupler acts as a valve and prevents deflation of each compartment.

After satisfactory placement of the device in the joint, the internal compartments can be test-inflated with air to check for proper function of the device and proper flexion of the joint. The air can then be removed and a radiopaque rubber or gel elastomer injected into the compartments. The preferred substance loses its fluidity and gels to provide structural support while retaining its cushioning properties. The elastomer and the prosthetic device thereby becomes suitably firm without becoming hard or brittle. In this fashion, the elastomer and the device retain the original shape, even if the tough outer membrane or reinforced internal compartments wear or otherwise fail. If wear or failure does occur, the health of the patient or other properties of the joint change, or the overall clinical situation warrants, the device can be removed or replaced. Since the elastomer is preferably radiopaque, intraoperative x-rays as well as outpatient x-rays can be used to confirm the correct angulation and fit. Additionally, an arthroscope equipped with a laser tip can be used to reduce the size of the prosthesis to facilitate its removal and subsequent replacement.

The articular surfaces can most preferably be comprised of a polypropylene or polyurethane polymer, which allow the joint to move freely yet supports the weight of the patient as appropriate. The internal compartments of the prosthesis can be independently inflated through a valve system to adjust both length and height as well as tilt, thus helping to compensate for medial and lateral compartment narrowing.

To implant the device described herein, arthroscopic surgical techniques can be used as mentioned above. The device is inserted through a channel with the arthroscope, and positioned by the scope with the joint. The prosthesis can be attached to the arthroscope by means of a clamp which is released once the placement of the device is suitable to the physician. Alternatively, when the device is inflatable or expandable, it can be attached to the scope via the tube and coupler valve system, which allows inflation of the chamber or chambers. A simple twisting action can release the prosthetic device from the scope after the chambers have been properly expanded with the radiopaque material described above.

Alternatively, the device can be equipped with an external lip or tab (not shown) which is attached to the arthroscope prior to and during surgical implantation. Prior to withdrawal of the scope and completion of the surgical procedure, the tab is typically cut or otherwise removed to avoid complications post surgically.

While the preferred embodiments of the invention have been described in detail herein, numerous alternative embodiments are contemplated as falling within the scope of the claims. Consequently, the claims are not limited to the specific embodiments recited herein.

What is claimed is:

1. An arthroscopically implantable prosthetic device for implantation into an angulating mammalian joint, said device being comprised of a collapsed expandable member, comprising means for the arthroscopic implantation thereof, said collapsed expandable member having valve means, adapted to permit the expansion of said member, by connection of the valve means to filling means, while said member is within said joint, whereby, with said expansion, the collapsed expandable member assumes a configuration of at least one annularly-shaped ring, sized and shaped to fit within said joint, and into direct contact with the joint, without said prosthetic device being attached to the joint, said valve means being fully contained within said joint, when disconnected from the filling means; said member being comprised of a polymeric material which is biocompatible to said joint and which allows said angulating joint to flex without substantial irritation, and wherein said ring has sufficient rigidity and free movement to withstand flexing of the joint.

2. The arthroscopically implantable prosthestic device of claim 1 comprised of a pair of annularly-shaped rings joined to each other laterally.

3. The arthroscopically implantable prosthestic device in accordance with claim 1, wherein
said ring contains at least one compartment which can be filled by said filling means, with a substance to expand said compartment after said implantation and during use, whereby said ring has sufficient rigidity and free movement to withstand flexing to provide structural support to the angulating joint.

4. The arthroscopically implantable prosthestic device for implantation into a mammalian joint in accordance with claim 3 comprised of a plurality of annularly-shaped rings, said rings being joined together and being sized in combination to fit within said joint, said rings being comprised of a polymeric material which is essentially non-irritating to said joint and the surrounding tissues and which allows said joint to flex without substantially irritation, said rings containing at least one compartment which can be filled with a substance to expand said compartment or to reduce the compressibility of said ring, and a means for filling said at least one compartment with said substance.

5. An arthroscopically implantable prosthestic device in accordance with claim 3 wherein said at least one compartment is fillable with a member of the group consisting of air, gas, water, liquid, a solid, a semi-solid and a gel which sets to form a semi-solid.

6. An arthroscopically implantable prosthestic device in accordance with claim 1 or 3 further comprised of a removable tab.

7. A method of alleviating joint pain in a mammalian patient comprising implanting into the joint an arthroscopically implantable device as described in claim 1.

8. An arthroscopically implantable prosthestic device for implantation into an angulating mammalian joint, the prosthetic device being comprised of a collapsed expandable member having means for the arthroscopic implantation thereof, within said joint; said collapsed expandable member having valve means adapted to permit the expansion thereof, while within said joint, with a fluid, whereby, with said expansion, the collapsed expandable member assumes a configuration of at least one annularly-shaped ring, sized and shaped to fit within said joint, and into direct contact with the joint, without said prosthetic device being attached to the joint, said member being comprised of a polymeric material which is biocompatible to said knee joint and which allows said joint to flex without substantial irritation, and wherein said ring has sufficient rigidity and free movement to withstand flexing of the joint, and wherein said at least one ring is further comprised of an abrasion-resistant, fiber-reinforced membrane.

9. An arthroscopically implantable prosthestic device in accordance with claim 8 wherein said at least one ring is comprised of a member of the group comprising of polyethylene, polypropylene, polyurethane and polybutyl rubber.

10. An arthroscopically implantable prosthestic device in accordance with claim 9 wherein said means for filling said at least one compartment is comprised of at least one line suitable for passing the substance into the compartment.

11. An arthroscopically implantable prosthestic device in accordance with claim 10 further comprised of an arthroscopic attachment means.

12. An arthroscopically implantable prosthestic device for implantation into a mammalian knee joint, the prosthetic device being comprised of a collapsed expandable member having means for the arthroscopic implantation thereof, within said knee joint; said collapsed expandable member having valve means to permit the expansion thereof, while within said knee joint, with a fluid, whereby, with said expansion, the collapsed expandable member assumes a configuration of at least one annularly-shaped ring, sized and shaped to fit within said knee joint, and into direct contact with the knee joint, without said prosthetic device being attached to the knee joint, said member being comprised of a polymeric material which is biocompatible to said knee joint and which allows said knee joint to flex without substantial irritation, and wherein said ring has sufficient rigidity and free movement to withstand flexing of the knee joint.

* * * * *